US 6,539,790 B2

(12) United States Patent
Huston et al.

(10) Patent No.: US 6,539,790 B2
(45) Date of Patent: Apr. 1, 2003

(54) STICTION-BASED CHUCK FOR BULGE TESTER AND METHOD OF BULGE TESTING

(75) Inventors: Dryver R. Huston, Burlington, VT (US); Wolfgang Sauter, Burlington, VT (US); Peter A. Sonntag, Starnberg (DE)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 10/006,259

(22) Filed: Dec. 4, 2001

(65) Prior Publication Data

US 2002/0066311 A1 Jun. 6, 2002

Related U.S. Application Data

(60) Provisional application No. 60/251,064, filed on Dec. 4, 2000.

(51) Int. Cl.[7] ............................................... G01N 3/10
(52) U.S. Cl. ..................................................... 73/150 A
(58) Field of Search ............................. 73/150 A, 842, 73/827, 807, 849

(56) References Cited

U.S. PATENT DOCUMENTS

| 4,833,920 A | * | 5/1989 | Knecht et al. ........... 361/283.3 |
| 4,851,497 A | * | 7/1989 | Wakui et al. ............... 524/601 |
| 4,899,581 A | * | 2/1990 | Allen et al. .............. 73/150 A |
| 6,050,138 A |   | 4/2000 | Lynch et al. ............. 73/150 A |

* cited by examiner

Primary Examiner—Max Noori
(74) Attorney, Agent, or Firm—Downs Rachlin Martin PLLC (57) ABSTRACT

A bulge tester (20) for determining residual stresses, and mechanical, thermal and other properties of a thin film (26) of material. The bulge tester includes a chuck (22) that supports the substrate (24) on which the film is deposited by stiction rather than through the use of mounting waxes, adhesives and mechanical clamping. The stiction inducing media (52) may be viscous grease, a flexible sheet of material such as a rubber, an elastomer, both or other materials. Bulge testing performed using the stiction-based chuck involves inducing stiction between the base (42) of the chuck and substrate of at least at least 1 kPascal (0.69 lb/in$^2$), as determined using a corner peel test. The pressurized fluid is delivered to the film to be tested, and materials properties of the film are determined as a function of pressure of the fluid and deflection of the film.

36 Claims, 5 Drawing Sheets

STICTION-BASED CHUCK FOR BULGE TESTER AND METHOD OF BULGE TESTING

RELATED APPLICATION DATA

This application claims the benefit of U.S. Provisional Patent Application No. 60/251,064, filed Dec. 4, 2000.

The invention described herein was funded in part by a National Science Foundation grant administered through the Vermont EPSCoR program, contract number EPS-9874685.

FIELD OF THE INVENTION

The present invention relates to systems and method reforming bulge testing of thin films and coatings of the type used in the semiconductor and optical industries, in the manufacture of microelectricalmechanical systems (MEMS), and in other contexts, and in particular to a chuck for supporting a substrate being tested and a method of using the chuck.

BACKGROUND OF THE INVENTION

Thin films are used in a de array of products, including integrated circuit devices, optical coatings, storage media, LCD matrix arrays, cutting tools, wear-resistant coatings, sensor arrays, and MEMS. The terms "thin film" and "film" are used to encompass films, coatings and layers of various thickness that are deposited on a substrate. These thickness typically range from 100 nanometers (nm)–5,000 nm, although include the range 10 nm–500,000 nm. Typically, each thin film has different residual stress characteristics and different thermal and/or mechanical properties, which may affect the performance, reliability, or durability of devices including or made using such thin films. It is often necessary to determine these materials properties in connection with research and development, manufacturing process development and control, and testing in volume manufacturing of devices including or made using thin films. Bulge testing is one technique for acquiring information concerning characteristics and properties of thin films.

Known prior art bulge systems, e.g., systems of the type described in U.S. Pat. No. 6,050,138 to Lynch et al. ("the '138 patent"), which is incorporated herein by reference, involve the use of a substrate having one or more apertures covered by the thin film to be bulge tested. Often the substrate is a silicon wafer of the type used in the manufacture of semiconductor devices, although other substrates may be used. In some cases, the apertures in the substrate are covered by a membrane or other layer of material and the thin film to be tested is deposited on such membrane or layer. The substrate is supported on a chuck and pressurized fluid, typically a gas but sometimes a liquid, is delivered via one or more orifices in the fixture to the region of the wafer where the apertures are located. The pressurized fluid causes the film, or the film and underlying membrane, to bulge, and then the materials properties may be determined as a function of the applied pressure and resultant deflection.

Existing bulge testing systems of the type described in the '138 patent represent an important advance in the art. However, the chucks used in these systems to support the substrate suffer from an important weakness that adversely affects precise determination of the desired characteristics and properties of the thin film being tested. In particular, known bulge testers secure the substrate to the chuck using equipment and/or materials that can introduce variable and unknown stresses, that may change with time into the thin film. For example, in one embodiment of the '138 patent, the substrate is attached to the chuck using a mounting wax, e.g., Crystal Bond™ polymer available from Electron Microscopy Sciences, Fort Washington, Pa. Other embodiments of the '138 patent involve mounting the substrate to the chuck using epoxies and cyanoacrylate adhesives and mechanical clamping techniques.

In addition to introducing variable and unknown stresses, equipment and materials of the type disclosed in the '138 patent suffer from other problems. It tends to be difficult to quickly and easily remove the substrate from the chuck in a way that does not leave behind residues that could adversely impair the operation of the thin film. For example, as noted in the '138 patent, when epoxies and cyanoacrylate adhesives are used, removal by heat decomposition leaves undesirable carbon residues behind. Also, dissolution of such materials in solvents such as acetone is very slow and leaves an organic residue that could alter the response of the thin film and hence impair analysis of its properties and impair further processing, such as the addition of more thin film layers or devices. While a substrate attached to a chuck with mounting wax can be removed with less difficulty than epoxies and cyanoacrylate adhesives, the removal process nevertheless takes time as it involves heating the wax until it becomes flowable. With mechanical clamping devices, as noted in the '138 patent, it tends to be difficult to reproducibly clamp the substrate. Also, hermetic sealing of the substrate adjacent the aperture region containing the film to be tested can be difficult to achieve with mechanical systems.

SUMMARY OF THE INVENTION

One aspect of the invention is a chuck for supporting a substrate to be used in bulge testing a film using pressurized fluid provided by a source. The substrate has an aperture and a film covering the aperture. The chuck comprises a base having a first surface and a media on the first surface for contacting and inducing stiction with the substrate. The stiction is induced such that as a result of the stiction alone a force of at least 1 KPascals is required to separate a 2.54 cm by 2.54 cm square portion of a silicon wafer from the media, as measured at one of the corners of the square portion in connection with peeling the corner away from the substrate.

Another aspect of the invention a system for bulge testing a film using pressurized fluid provided by a source. The system comprises a substrate having an aperture with a film covering the aperture, a base having a first surface and a viscous media on the first surface for contacting the substrate. The viscous media creates stiction with the substrate and remains viscous at room temperature for extended periods of time.

Yet another aspect of the invention is a bulge test system for testing a portion of a film of material positioned on a substrate having an aperture positioned adjacent the film. The system comprises a source of pressurized fluid and a device for determining deflection of the film portion being bulge tested and providing a first output signal containing information representative of the extent of deflection of the film portion. In addition, the system includes a base having a first surface and a media on the first surface for contacting the substrate. The media induces stiction with the substrate such that a force of at least 1 KPascals is required to separate a 2.54 cm by 2.54 cm square portion of a silicon wafer from the media as measured at one of the four corners of the portion in connection with peeling the corner away from the substrate.

Still another aspect of the present invention is a method of bulge testing a film. The method involves providing a substrate with an aperture and a film extending over the aperture. Next, stiction is induced between the substrate and the surface such that a force of at least 1 KPascals is required to separate a 2.54 cm by 2.54 cm square portion of a silicon wafer from the media as measured at one of the corners of the portion in connection with peeling the corner away from the substrate. Then, a pressurized fluid is directed through the aperture so as to contact the film and cause it to deflect. Material properties of the film are then determined as a function of pressure of the fluid and deflection of the film.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE INVENTION

Figure 1:
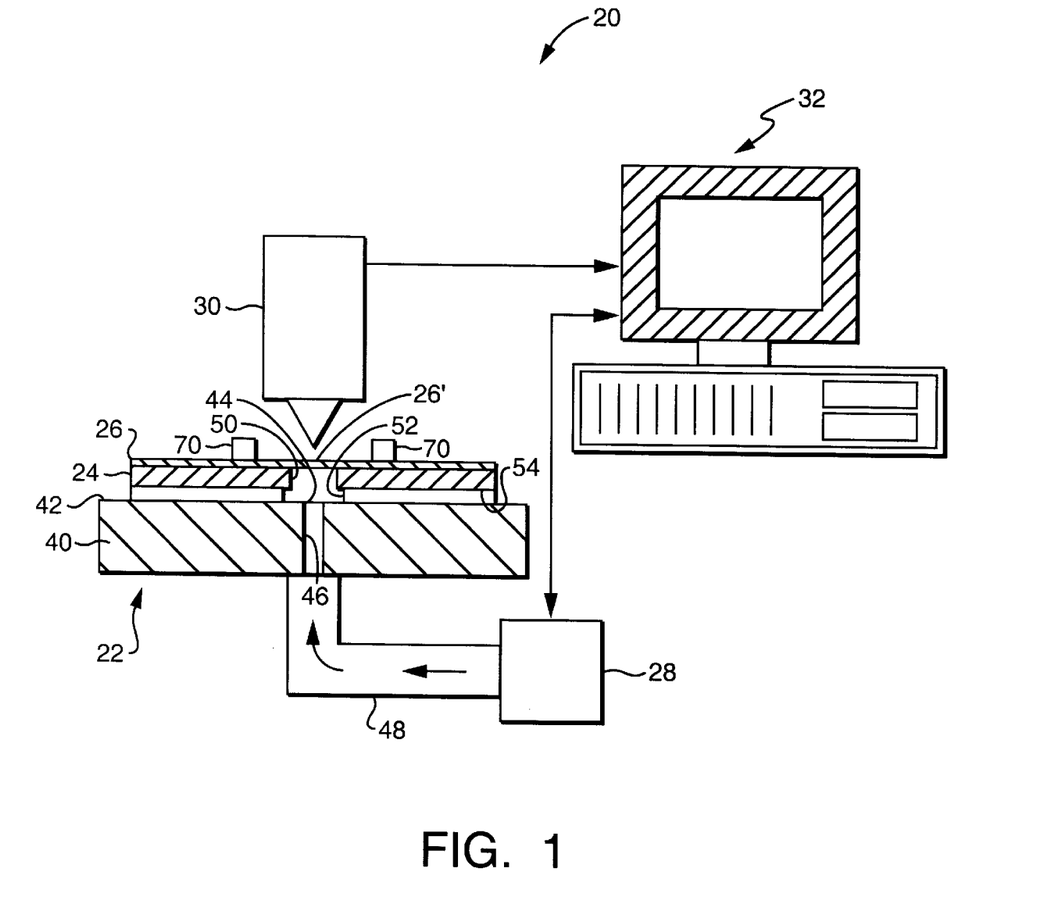
FIG. 1 is a schematic diagram of the bulge testing system of the present invention, with the chuck of the system being shown in cross-sectional view taken along line 1—1 in FIG. 3.
Figure 2:
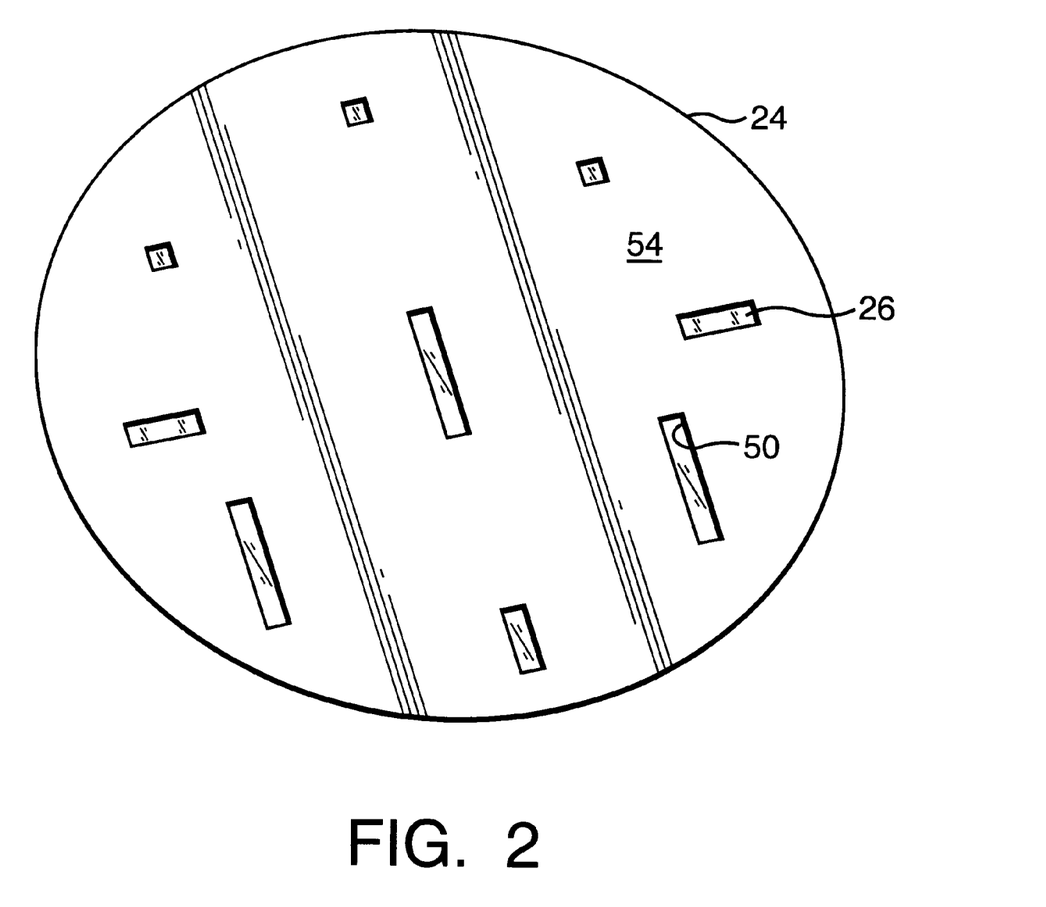
FIG. 2 is a perspective bottom view of a substrate used in connection with the system shown in FIG. 1.

Referring now to the drawings in which like reference numerals indicate like parts, and in particular to FIGS. 1 and 2, the present invention is a bulge tester 20 and a method of bulge testing films. Bulge tester 20 is similar to known bulge testers with the exception of its chuck 22, which is described in more detail below. Briefly, however, chuck 22 holds a substrate 24 having a film 26 to be tested with stiction, rather than securing the substrate to the chuck with adhesives, waxes, mechanical clamping or other known techniques. Film 26 is described in more detail below in connection with a description of the method of bulge testing using tester 20. The relative thicknesses of substrate 24 and film 26, along with base 40 and media 52 which are discussed below, are not necessarily shown in proper scale in the drawings.

Like known bulge testers, tester 20 includes a pressure source 28 for providing pressurized fluid and determining the pressure of the fluid, e.g., using a pressure transducer (not shown). The fluid may be a gas, such as air, or a liquid, such as water. Pressure source 28 may provide the fluid at negative or positive pressures.

Tester 20 also includes a deflection measurement device 30 for measuring deflection of film 26. Device 30 provides an output signal containing information representative of the extent of deflection of the portion of film 26 being tested. Pressure source 28 and device 30 are connected to computer 32. The latter is used to control the operation of pressure source 28, and determine properties of film 26 based on pressure information contained in the output signal of pressure source 28 and deflection information contained in the output signal of deflection measurement device 30. Although not illustrated, chuck 22 is preferably mounted on an X-Y-Z stage connected to computer 32 that adjusts the position of chuck 22, and hence support 24 and film 26, relative to device 30.

For a more detailed description of pressure source 28, deflection measurement device 30 and computer 32, attention is directed to the description of the comparable elements of the bulge tester described in the '138 patent, which is incorporated herein by reference. With the exception of the manner in which substrate 24 is held by chuck 22, as discussed below, the method of operating bulge tester 20 and determining properties of film 26 may be the same as that described in the '138 patent relative to the bulge tester described therein. Bulge tester 20 and the method of performing bulge testing using tester 20 may also be performed using components other the ones specifically identified in the '138 patent in connection with the description of pressure source 28, deflection measurement device 30 and computer 32, as known to those skilled in the art.

Figure 3:
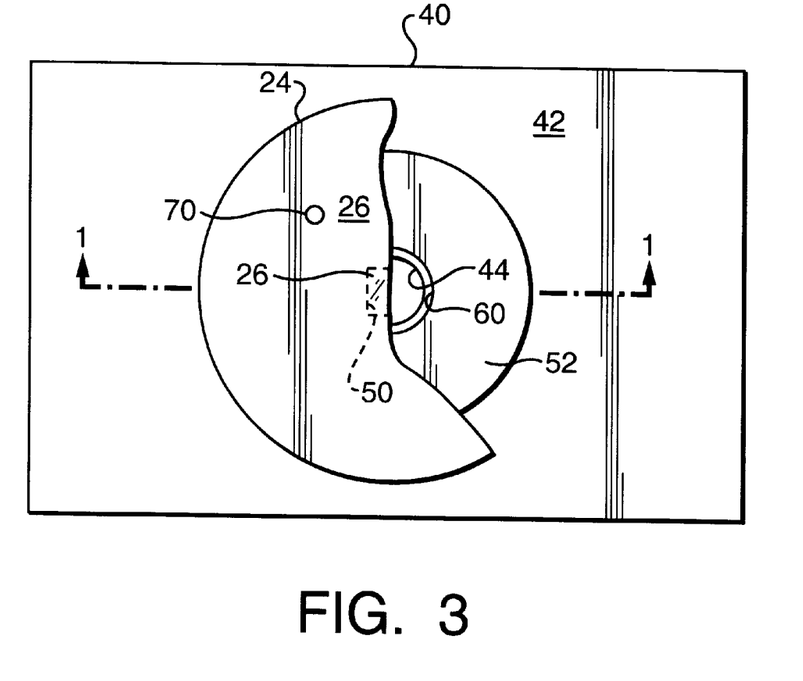
FIG. 3 is a top view of the chuck of the system of FIG. 1, with the substrate of FIG. 2 being positioned on the surface of the chuck, and with a portion of the substrate being broken away to reveal the stiction media position between the substrate and the surface.

Turning now to FIGS. 1–3, in one embodiment, chuck 22 includes a base 40 having a first surface 42. Base 40 may be made from a range of materials, including metals, e.g., steel or aluminum, wood, plastics, composites and the like. Factors such as durability, hardness, attraction to a magnet, ability to produce first surface 42 so that it has the desired degree of smoothness, and the embodiment of the invention with which chuck 22 is used, all as described below, will influence the choice of material for the chuck.

As illustrated in FIG. 1, first surface 42 is the top surface of base 40. Because chuck 22 may be positioned with first surface 42 down relative to the horizon, or in other spatial relationship to the horizon, as described in more detail below, first surface 42 is not necessarily the top surface of the chuck.

Base 40 includes opening 44, which is connected via passageway 46 to a tube 48 or other structure capable of transporting a pressurized fluid. Tube 48 in turn is connected to pressure source 28. Opening 44 is positioned in surface 42 so as to be alignable with aperture 50 of substrate 24, as illustrated in FIG. 1 and described in more detail below.

Chuck 22 includes media 52 positioned on all or a portion of first surface 42, between the first surface and bottom surface 54 of substrate 24. In one embodiment of the invention media 52 is a viscous grease, such as a high-vacuum grease, e.g., the silicone high-vacuum grease sold by Dow-Corning Corp. of Midland, Mich., and identified by part no. 1583191 0978. Typically, viscous grease used as media 52 has a stiffness as specified by NLGI (National Lubricating Grease Institute) Grade 0 to 6 or a viscosity in the range 10 to 1,000 mPa-s (milliPascal-second) at room temperature. Viscous grease suitable as media 52 differs from mounting waxes and adhesives such as epoxies used in the chucks of known bulge test equipment in that it remains viscous at or around room temperature for extended periods of time. Mounting waxes are not typically viscous at room temperature, they are solid, and adhesives, which may be temporarily viscous at room temperature, do not retain such viscosity for extended periods of time.

When media 52 is a viscous grease, it is preferred that first surface 42 of base 40 be machined so as to be very smooth. The desirability of a smooth surface will influence the choice of materials for base 40, with materials that can be quickly and easily machined so as to achieve and maintain a smooth first surface 42 being preferred.

When media 52 is viscous grease, the type and viscosity of grease used is selected to induce sufficient stiction between base 40 and substrate 24 to achieve a reasonably air-tight seal, preferably but not necessarily a hermetic seal, between the portion of the substrate adjacent aperture 50 and the base. This stiction force is preferably at least 1 kPascal (0.69 lb/in$^2$) as determined using a corner peel test with a substantially square 2.54 cm×2.54 cm piece of a conventional silicon semiconductor wafer. having a thickness of about 0.3 mm to 0.8 mm, typically about 0.5 mm and strong enough to peel without breaking. The viscous grease is spread on first surface 42, the square wafer piece is pressed into the viscous grease, a corner of the piece is lifted up and the force required to lift up the corner is measured. While a stiction force of at least 1 KPascals is desired, the present invention encompasses stiction forces in the range of 1–30 kPascals (0.69–20.7 lb/in$^2$). In one test performed using chuck 22, a 2.54 cm by 2.54 cm square piece of a conventional silicon semiconductor wafer, and the Dow-Corning high-vacuum silicone grease discussed above, which was applied to a thickness of about 0.5 mm, a stiction of about 4 kPascals was induced with media 52, as determined by the above-described corner peel test.

The degree of smoothness of first surface 42 will influence the choice of viscous grease, with less smooth surfaces requiring the use of a viscous grease capable of inducing greater stictional forces than the viscous grease used with highly smooth surfaces. Maximum stiction is typically achieved when the entire surface 54 of substate 24 is in contact with the viscous grease. In some cases, however, as illustrated in FIG. 1, the viscous grease need contact only a portion of surface 54. The stiction forces to be induced by the viscous grease under the intended bulge test procedure, the pressure at which fluid is delivered by pressure source 28, the desirability of minimizing the area from which the grease needs to be removed, e.g., in connection with subsequent processing of the substrate, the orientation of chuck 22 relative to the horizon and the related influence of gravity on the substrate, the surface adhesion and wet-ability of the substrate, and other factors will influence the extent of surface 54 contacted by the viscous grease and the viscosity of the grease selected. Those skilled in the art will appreciate how to weigh these and other factors, theoretically and through empirical testing, in connection with selecting the optimal grease to be used.

While the term "grease" has been used to describe this embodiment of media 52, the term is not meant to impose limitations as to the materials used. Thus, any material capable of inducing the stiction forces described above and retaining its viscosity at room temperatures for extended periods of time is encompassed by the term "grease." This definition of "grease" is intended to differentiate media 52 from mounting waxes, which are not viscous at room temperature, and adhesives such as epoxies, which do not remain viscous at room temperature for extended periods of time, i.e., they harden in a relatively short period of time. However, it is not intended to restrict the materials that may be used as the grease. Indeed, virtually any material that is liquid at the temperatures where bulge testing will be performed and is capable of inducing the stiction discussed above may be used, with the factors discussed in the preceding paragraph, among others, influencing the choice of materials.

In another embodiment of the invention, media 52 is a piece of relatively soft material. The thickness, durometer, surface characteristics and other attributes of the material are selected so as to induce stiction between the material and substrate 24 sufficient to create a reasonably air-tight seal, preferably but not necessarily a hermetic seal, between the portion of the substrate adjacent aperture 50 and base 40. As described above with respect to the viscous grease, this stiction is preferably at least 1 kPascal (0.69 lb/in$^2$), as determined using the corner peel test described above, and may range from 1–30 kPascals (0.69–20.7 lb/in$^2$). In some cases it may be desirable to attach the material to surface 42 of base 40 using adhesives or other materials or techniques. One choice of soft material for media 52 is a sheet of natural or synthetic rubber having a thickness in the range of 0.5 to 5 mm and a Shore durometer in the range 25 to 95, more preferably in the range 40 to 60. Other suitable materials include elastomers, polymers, solid foams with smooth skins and other solids with sufficient flexibility, surface smoothness and surface adhesion to form a reasonably air-tight seal between the wafer and the solid. As when viscous grease is used as media 52, the piece of material used as media 52 may cover some (as shown in FIG. 1) or all of surface 54, or may even extend beyond the periphery of the substrate. An opening 60 (see FIG. 3) is formed in media 52 adjacent opening 44 so as to permit direct fluid communication between the opening and the portion of substrate 24 adjacent the opening.

If desired, media 52 may comprise both the flexible material and viscous grease. The viscous grease is positioned between the flexible material and substrate 24.

In some cases, e.g., where the stiction induced by media 52 is insufficient or minimally sufficient to hold substrate 24 on base 40, it may be desirable to use one or more magnets 70 positioned on film 26, as illustrated in FIG. 1. In such case, base 40 should be made from a ferromagnetic material. The magnetic attraction between magnets 70 and base 40 may, in some cases (e.g., when pressurized fluid is delivered by pressure source 28 at a negative pressure), retain substrate 24 in sufficient engagement with first surface 42 of base 40 that media 52 is not required. Sufficient engagement is generally achieved, as discussed above, when a reasonably air-tight seal, preferably but not necessarily a hermetic seal, is achieved between substrate 24 and base 40 adjacent opening 60.

Figure 4:
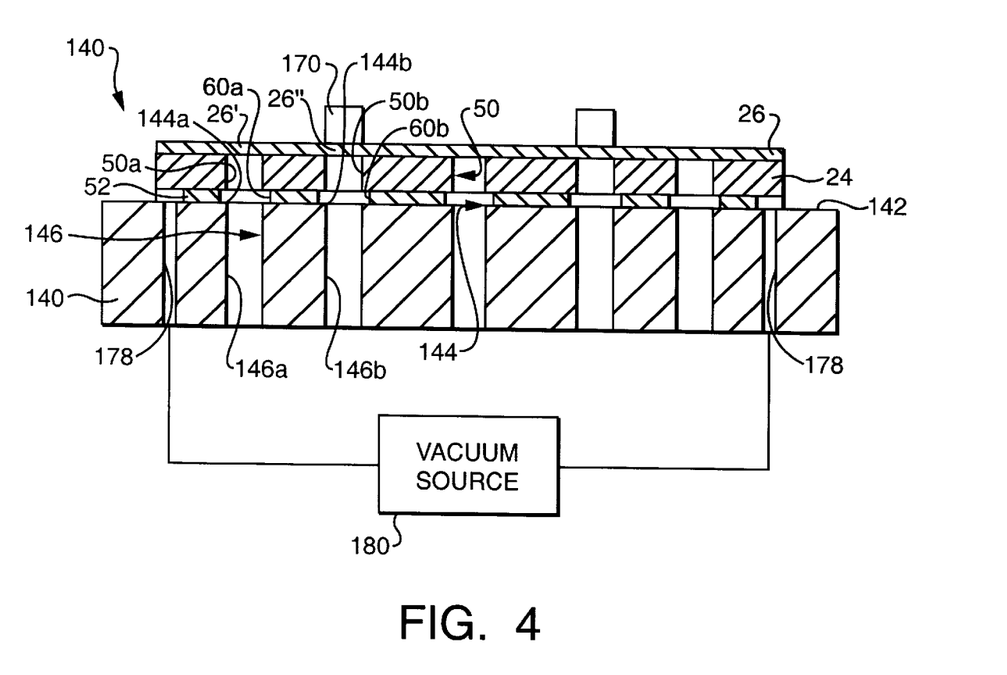
FIG. 4 is a cross-sectional view of an alternative embodiment of the chuck of the present invention taken along line 4—4 in FIG. 5.
Figure 5:
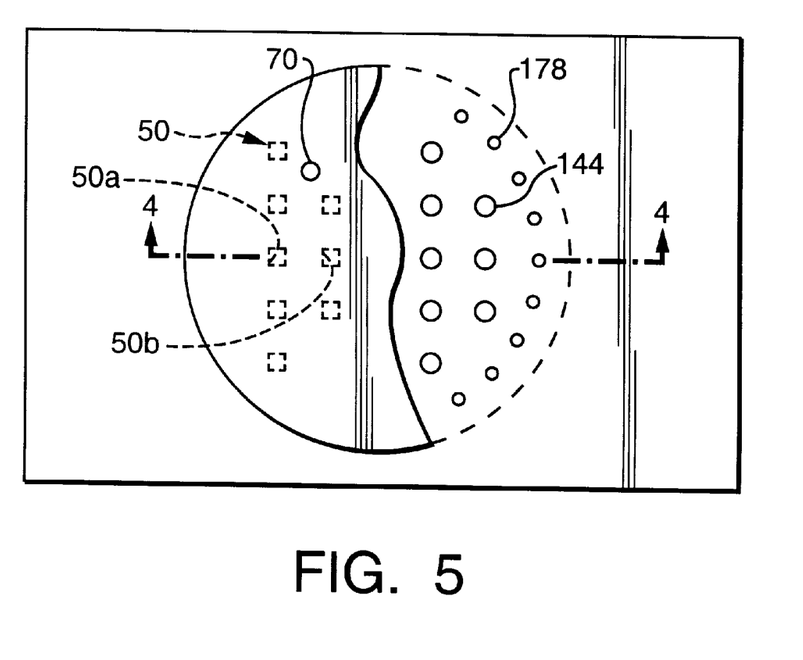
FIG. 5 is a top view of the chuck of FIG. 4, with the substrate of FIG. 2 being positioned on the surface of the chuck, and with a portion of the substrate being broken away to reveal the stiction media position between the substrate and the surface.

Referring now to FIGS. 1, 4 and 5, in some cases it may be desirable to perform simultaneous or sequential bulge testing with respect to more than one portion of film 26 on substrate 24. To achieve such testing, multiple apertures 50 are provided in substrate 24, e.g., apertures 50a and 50b. Each aperture 50 is covered with a portion of film 26 to be tested. Of course apertures 50 may be provided in substrate 24 that are not covered with film 26, and not all the apertures covered with the film need be bulge tested.

In another embodiment of the present invention, chuck 122 is provided for performing such bulge testing of multiple portions of film 26 on substrate 24. Elements of chuck 122 that are identical to corresponding elements of chuck 22 are numbered identically, except that a 100's series prefix is used, e.g., chuck 122 instead of chuck 22. Base 140 includes a plurality of openings 144 in first surface 142, each in fluid communication with a corresponding passageway 146. For example, opening 144a is in fluid communication with passageway 146a, opening 144b is in fluid communication with passageway 146b, and so on. As shown in FIG. 1 with respect to passageway 46, each passageway 146 is connected via a tube 48 to pressure source 28. In some cases it may be desirable to use a distribution manifold between pressure source 28 and each passageway 146. Pressurized fluid may be provided simultaneously to each passageway 146 from pressure source 28. Alternatively, the pressurized fluid may be provided sequentially to one or groups of passageways 146. In the latter case, it may be desirable to provide a valve in each tube 48 for controlling when pressurized fluid is provided to a passageway 146. Optionally, magnet 170 may be used with chuck 122.

As another optional feature of chuck 120, a plurality of vacuum ports 178 may be provided extending through base 140 to first surface 142. Vacuum ports 178 are connected to a vacuum source 180. The negative pressure drawn by vacuum source 180 and provided at first surface 142 via vacuum ports 178 holds substrate 24 to the first surface. Vacuum ports 178 may also be provided in chuck 22 (not shown).

In general, it is not preferred to support substrate 24 on chucks 22 or 122 by vacuum pressure as undesirable and variable stresses are introduced in film 26 as a consequence of the vacuum pressure. However, in some cases the stiction-based chucks of the present invention may be used successfully to perform bulge testing of films on a substrate held to the chuck with vacuum pressure. Vacuum pressure can be used to induce a supplemental holding force when the stiction induced by media 52 is insufficient or minimally sufficient. Typically, vacuum pressure is used as an alternative to magnets 70 and 170, although the invention encompasses the use of both vacuum pressure and magnets.

When multiple portions of film 26 on substrate 24 are to be bulge tested an aperture 50 is provided adjacent each portion. For example, aperture 50a is provided adjacent film portion 26' and aperture 50b is provided adjacent film portion 26". Additionally, a plurality of openings 60 is provided in media 52 adjacent each aperture 50, e.g., opening 60a adjacent aperture 50a and opening 60b adjacent aperture 50b.

In FIG. 5 the region enclosed by the broken-away edge of substrate 24 and the dotted line is intended to represent media 52 in the form of viscous grease. In some cases, the viscous grease will only be positioned adjacent opening 144 and in other cases it will extend to the dotted line, as indicated.

Figure 6:
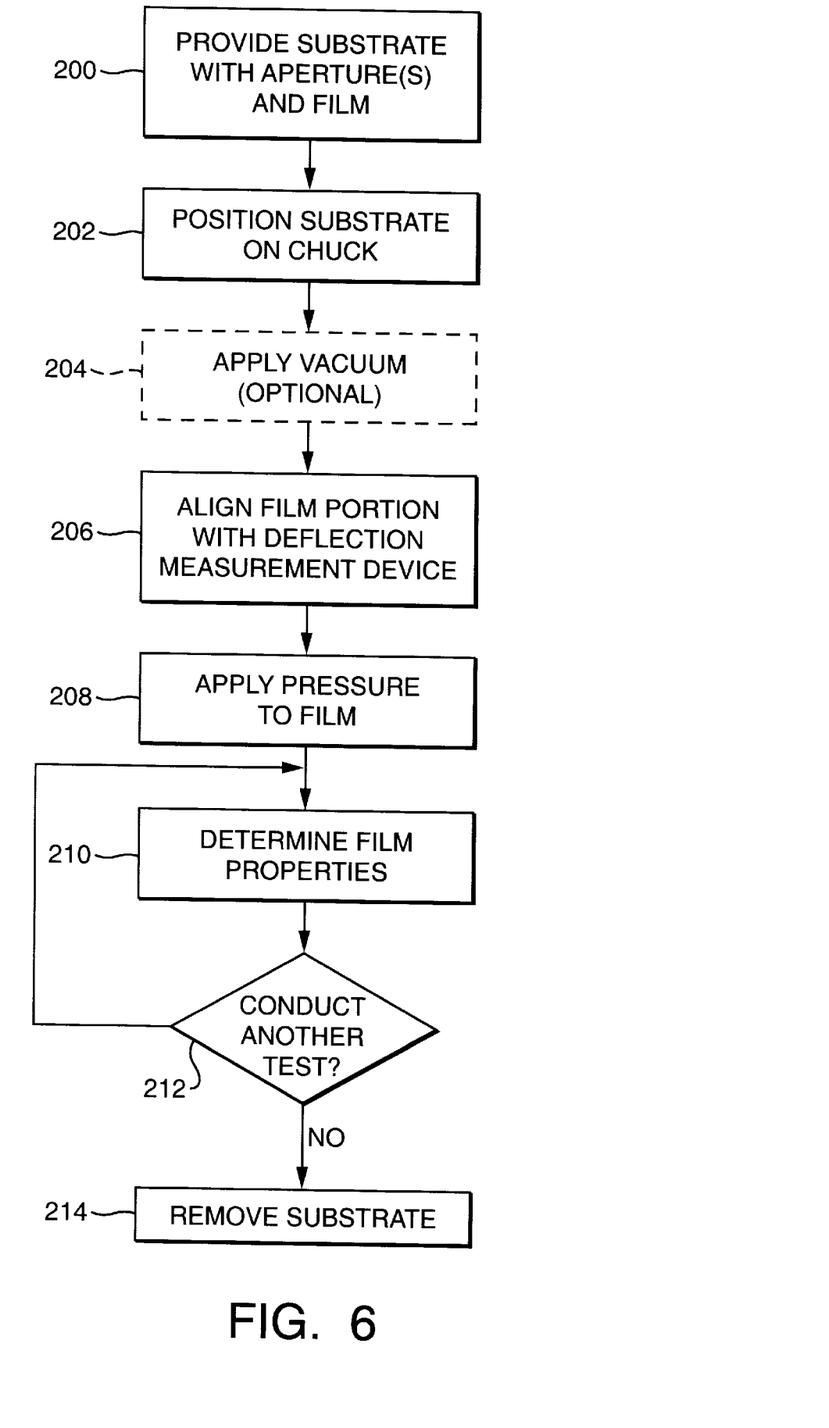
FIG. 6 is a flow diagram of the bulge testing method of the present invention.

Turning now to FIG. 6, with incidental reference to FIGS. 1–5, bulge testing may be performed using tester 20 with chuck 22 in the following manner. First, as first step 200, a substrate 24 having a film 26 is provided. Film 26 may, in its entirety, be the film to be tested, or may comprises a two-layer film, with the lower layer (i.e., the layer contacting or closest to substrate 24) being a membrane and the upper layer being the film to be tested. The membrane is preferably made of a material that is free of residual stresses and is easy to make and characterize, e.g., semiconductor-grade single crystal silicon. This two-part film layer is described in more detail in the '138 patent. The portion of film 26 to be tested covers all or part of an aperture 50 in substrate 24.

The term "film 26" as used herein means a film, coating or layer of the type composed of metals (e.g., Ni, Au, Ag), paint, dielectric thin films, organic compounds or polymers (e.g., photoresists), hard coatings, ceramics (e.g., silicon nitride) and other materials. Film 26 generally has a thickness in the range 10 nm–500,000 nm, and more typically in the range from 100 nm–5,000 nm.

Next, at step 202, substrate 24 is positioned on media 52 on first surface 42 of base 40 so that aperture 50 is aligned with passageway 46 (see FIG. 1). As a consequence of the stiction induced by media 52, substrate 24 is held to chuck 22 with sufficient force to perform satisfactory bulge testing using known techniques. In this regard, as noted above, the stiction media 52 induces is at least 1 kPascal (0.69 lb/in$^2$) as determined using the above-described corner peel test. In many cases chuck 22 will be oriented so that substrate 26 is above base 40, with gravity pulling the substrate against the base along an imaginary axis extending perpendicular to first surface 42. However, in some cases it may be desirable to orient chuck 22 so that its first surface 42 extends transversely to the pull of gravity. In addition, chuck 22 may be oriented upside down so that gravity pulls substrate 26 away from base 42.

If chuck 22 includes vacuum ports 178, and it is desired to apply vacuum pressure to substrate 24, then vacuum source 180 is activated and a vacuum is created at surface 42, as indicated by step 204. As desired, vacuum source 180 may be deactivated immediately after substrate 24 is drawn against surface 42, or may remain activated during subsequent processing steps.

At step 206, the portion 26' of film 26 to be tested is aligned with deflection measurement device 30. This may be achieved manually or automatically through use of an x-y-z stage (not shown) coupled with base 40 and/or device 30.

Then, at step 208, pressure source 28 is activated so as to apply pressurized fluid through tube 48 and passageway 46 to opening 44. The pressurized fluid then travels through aperture 50 in substrate 24 until it reaches film portion 26' above aperture 50. The pressurized fluid causes portion 26' to bulge. Air and other inert gases may be used as the pressurized fluid, as may liquids such as water and other liquids that do not react with chuck 22, substrate 24 and film 26. The pressurized fluid is generally provided at a pressure of 0.1 to 40 kPascals (0.07 to 5 lbs/in$^2$), with about 2 to 7 kPascals (0.17 to 0.6 lbs/in$^2$) being preferred. In many cases it is preferable to provide the fluid at a positive pressure. However, providing the fluid at a negative pressure may also be desirable, and may reduce the stiction force that media 52 must be capable of inducing. This is so because the negative pressure drawn at aperture 50 will generally increase the tendency of substrate 24 to develop a reasonably air-tight seal with first surface 42 of base 40. Thus, selection of the pressure to be applied at step 208 must be chosen in view of the stiction forces media 52 is capable of inducing.

Next, at step 210, selected properties of film portion 26' are determined using known techniques based on the deflection of the film portion detected by deflection measurement device 30. These properties include, without limitation, residual stress characteristics, thermal and/or mechanical properties. Using deflection information provided by deflection measurement device 30 and known software programs, computer 32 determines the selected properties of film portion 26' in the manner described in the '138 patent.

While the present method has been described relative to bulge testing, it is to be appreciated the invention may also be used for blister testing. With blister testing the pressure of the fluid delivered by pressure source 28 is selected so that instead of causing film portion 26' to merely bulge, the film is caused to delaminate from substrate 24. Information contained in the output signal of deflection measurement device 30 can be used to determine adhesion properties of film portion 26', as is known to those skilled in the art. Thus, use of the term "bulge tester" in connection with bulge tester 20 should not be considered as limiting use of the tester to bulge testing since it can also be used for blister testing.

At step 212 a determination is made whether another bulge test should be conducted. When substrate 24 includes only one film portion 26' to be tested in some cases one test is enough and in other cases repeat testing is desired. If another bulge test is to be conducted, the process loops back to step 210 and the selected film properties are determined again. It may be desirable to loop back to step 208 and provide a new pressurized fluid application before determining the film properties again.

While up to this point the process of bulge testing has been described relative to chuck 22, the steps are identical for chuck 122. However, when chuck 122 is used with multiple film portions 26', then it is the inquiry at step 212 that initiates performance of the bulge test at each film portion of interest. Typically, the relative positioning between deflection measurement device 30 and the film portion 26' to be bulge tested is adjusted when the inquiry at step 212 indicates another bulge test is to be conducted so as to achieve the desired alignment between the device and the film portion.

Eventually the determination at step 212 will indicate that no more bulge testing is to be performed. Then, substrate 24 is removed from chuck 22, as indicated by step 214.

Chucks 22 and 122 of the present invention possess a number of advantages over known chucks used in bulge testing. By avoiding introduction of stresses created by mounting waxes, mechanical clamping and other known techniques used to hold a substrate during bulge testing, more accurate results can be achieved.

Another advantage of the stiction-based support of substrate 24 is that the process of mounting the substrate on, and removing the substrate from, chuck 22 or 122 can generally be accomplished more quickly than mounting techniques involving the use of mounting waxes and adhesives. This is particularly advantageous when bulge testing is being performed as part of a test procedure in volume manufacturing of a product having a thin film. Further, when media 52 is a flexible sheet of material and substrate 24 is a silicon wafer or other substrate used in volume manufacturing, minimal if any clean up of the substrate is required after bulge testing. As a result, the substrate and be quickly reintroduced into the manufacturing process for subsequent processing steps. By contrast, removal of mounting waxes and adhesives can be problematic in volume manufacturing. To a lesser extent, the same is true of viscous greases.

While the present invention has been described in connection with a preferred embodiment, it will be understood that it is not so limited. On the contrary, it is intended to cover all alternatives, modifications and equivalents as may be included within the spirit and scope of the invention as defined in the appended claims.

What is claimed is:

1. A chuck for supporting a substrate to be used in bulge testing a film using pressurized fluid provided by a source, the substrate having an aperture with a film covering the aperture, the chuck comprising:

a) a base having a first surface; and
   b) a media on said first surface for contacting and inducing stiction with the substrate such that as a result of said stiction alone a force of at least 1 KPascals is required to separate a 2.54 cm by 2.54 cm square portion of a silicon wafer from said media, the portion having four corners, as measured at one of the corners in connection with peeling the corner away from the substrate, said media capable of being easily removed from said substrate upon completion of the bulge testing.

2. A chuck according to claim 1, wherein said base includes an opening extending through said first surface and a passageway in fluid communication said opening, said passageway countable to a source of pressurized fluid, said opening being positioned so as to be alignable with the aperture when the substrate is positioned in a first relationship to said first surface.

3. A chuck according to claim 1, wherein said media comprises a viscous grease.

4. A chuck according to claim 3, wherein said grease has a viscosity at room temperature ranging from 10 to 1,000 mPa-s (milliPascal-second).

5. A chuck according to claim 1, wherein said media comprises a piece of flexible material.

6. A chuck according to claim 5, wherein said flexible material has a Shore durometer ranging from 25 to 95.

7. A chuck according to claim 5, wherein said flexible material has a Shore durometer ranging from 40 to 60.

8. A chuck according to claim 1, wherein said media comprises a piece of flexible material and a viscous grease provided on said flexible material so as to contact the substrate.

9. A chuck according to claim 2, wherein said base comprises a plurality of openings extending through said first surface and a plurality of passageways each fluidly coupled with a corresponding respective one of said plurality of openings.

10. A chuck according to claim 1, wherein said base is made from a ferromagnetic material and said chuck further includes a magnet for urging the substrate toward said base when the substrate is positioned between said magnet and said base so as to contact said magnet.

11. A chuck according to claim 2, wherein said base includes a plurality of vacuum ports.

12. A system for bulge testing a film using pressurized fluid provided by a source, the system comprising:

a) a substrate having an aperture with a film covering the aperture;
   b) a base having a first surface; and
   c) a viscous media on said first surface for contacting said substrate and creating stiction with said substrate, said media remaining viscous at room temperature for extended periods of time, said media capable of being easily removed from said substrate upon completion of the bulge testing.

13. A chuck according to claim 12, wherein said viscous media has a viscosity such that as a result of said stiction alone a force of at least 1 kPascals is required to separate a 2.54 cm by 2.54 cm square portion of a silicon wafer from said media, the portion having four corners, as measured at one of the corners in connection with peeling the corner away from the substrate.

14. A chuck according to claim 10, wherein said viscous media has a viscosity ranging from 10 to 1,000 mPa-s (milliPascal-second).

15. A chuck according to claim 10, wherein said base includes an opening in said first surface and a passageway in fluid communication said opening, said passageway countable to a source of pressurized fluid, said opening being positioned so as to be aligned with the aperture when the substrate is positioned in a first relationship to said first surface.

16. A bulge testing system for testing a portion of a film of material positioned on a substrate having an aperture positioned adjacent the film, the system comprising:

a) a source of pressurized fluid;
   b) a device for determining deflection of the film portion being bulge tested and providing a first output signal containing information representative of the extent of deflection of the film portion;

c) a base having a first surface; and d) a media on said first surface for contacting the substrate, said media inducing stiction with the substrate such that a force of at least 1 KPascals is required to separate a 2.54 cm square portion of a silicon wafer from the media, the portion having four corners, as measured at one of the corners in connection with peeling the corner away from the substrate, said media capable of being easily removed from said substrate upon completion of the bulge testing.

17. A bulge test system according to claim 16, further including a computer connected to said device, said computer being programmed with software for determining properties of the film portion being bulge tested based on said information contained in said first output signal.

18. A system according to claim 16, wherein said media comprises a viscous grease.

19. A system according to claim 18, wherein said viscous grease has a viscosity ranging from 10 to 1,000 mPa-s (milliPascal-second).

20. A system according to claim 16, wherein said media comprises a piece of flexible material.

21. A system according to claim 20, wherein said piece of flexible material has a Shore durometer ranging from 40 to 60.

22. A system according to claim 16, wherein media comprises a piece of flexible material and a viscous grease provided on said flexible material so as to contact the substrate.

23. A method of bulge testing a film comprising the steps of:

a) providing a first surface, and a substrate with an aperture and a film extending over the aperture;

b) providing a media on said first surface for contacting the substrate;

c) inducing stiction between the substrate and the surface such that a force of at least 1 KPascals is required to separate a 2.54 cm by 2.54 cm square portion of a silicon wafer from the media, the portion having four corners, as measured at one of the corners in connection with peeling the corner away from the substrate, said media capable of being easily removed from said substrate upon completion of the bulge testing;

d) directing a pressurized fluid through said aperture so as to contact said film and cause it to deflect; and e) determining material properties of the film as a function of pressure of the fluid and deflection of the film.

24. A method according to claim 23, wherein said inducing step c) involves providing a piece of flexible material between the surface and the substrate, the material capable of inducing said stiction.

25. A method according to claim 23, wherein said inducing step c) involves providing a viscous grease between the surface and the substrate, the viscous grease capable of inducing said stiction.

26. A method according to claim 23, wherein said inducing step c) involves providing a piece of flexible material between the surface and the substrate and providing a viscous grease between the material and the substrate, the material and viscous grease capable of inducing said stiction.

27. A method according to claim 23, wherein said pressurized fluid is delivered at a pressure ranging from 0.1 to 40 KPascals.

28. A method according to claim 23, the substrate having a plurality of apertures, each with a film overlying the aperture, wherein the method further comprises the steps of directing the pressurized fluid through each of said plurality of apertures so as to contact the film overlying said each aperture and cause it to deflect, and then determining material properties for each film contacted by the pressurized fluid.

29. A method according to claim 23, further including the step of urging the substrate against the surface with vacuum pressure.

30. A method according to claim 23, further including the step of urging the substrate against the surface with magnetic force.

31. A method of supporting a film to be bulge tested comprising the steps of:

a) providing a substrate with an aperture and a film adjacent the aperture;

b) positioning the film on a surface; and c) including a media between the film and the substrate to induce stiction forces between the film and the surface such that a force of at least 1 KPascals is required to separate a 2.54 cm by 2.54 cm square portion of a silicon wafer from the media, the portion having four corners, as measured at one of the corners in connection with peeling the corner away from the substrate, the media capable of being easily remove from the substrate upon completion of the bulge testing.

32. A method according to claim 29, wherein said inducing step c) involves providing a piece of flexible material between the surface and the substrate, the material capable of inducing said stiction.

33. A method according to claim 29, wherein said inducing step c) involves providing a viscous grease between the surface and the substrate, the viscous grease capable of inducing said stiction.

34. A method according to claim 29, wherein said inducing step c) involves providing a piece of flexible material between the surface and the substrate and providing a viscous grease between the material and the substrate, the material and viscous grease capable of inducing said stiction.

35. A method according to claim 29, further including the step of urging the substrate against the surface with vacuum pressure.

36. A method according to claim 29, further including the step of urging the substrate against the surface with magnetic force.

* * * * *

UNITED STATES PATENT AND TRADEMARK OFFICE
CERTIFICATE OF CORRECTION

PATENT NO. : 6,539,790 B2 Page 1 of 1
APPLICATION NO. : 10/006259
DATED : April 1, 2003
INVENTOR(S) : Dryver R. Huston, Wolgang Sauter and Peter A. Sonntag It is certified that error appears in the above-identified patent and that said Letters Patent is hereby corrected as shown below:

(a) In claim 2, column 10, line 2, delete the word "countable" and insert --couplable-- therefor.

(b) In claim 15, column 10, lines 57/58, delete the word "countable" and insert -- couplable-- therefor.

(c) In claim 16, column 10, line 62, delete "testing" and insert --test-- thereof.

(d) In claim 16 d), column 11, line 8, after the words "to separate a 2.54 cm" insert --by 2.54 cm--.

(e) In claim 31 c), column 12, line 36, delete "remove" and insert --removed-- therefor.

Signed and Sealed this

Eighth Day of August, 2006

JON W. DUDAS
*Director of the United States Patent and Trademark Office*